United States Patent
Mukunda et al.

(10) Patent No.: US 10,933,082 B2
(45) Date of Patent: Mar. 2, 2021

(54) CANNABINOID COMPOSITION AND METHOD FOR TREATING PAIN

(71) Applicant: India Globalization Capital, Inc., Bethesda, MD (US)

(72) Inventors: Ramachandra Mukunda, Potomac, MD (US); Ranga Chelva Krishna, Englewood, NJ (US)

(73) Assignee: India Globalization Capital, Inc., Potomac, MD (US)

( * ) Notice: Subject to any disclaimer, the term of this patent is extended or adjusted under 35 U.S.C. 154(b) by 0 days.

(21) Appl. No.: 16/148,775

(22) Filed: Oct. 1, 2018

(65) Prior Publication Data

US 2019/0030062 A1 Jan. 31, 2019

Related U.S. Application Data

(62) Division of application No. 15/104,554, filed as application No. PCT/US2015/050342 on Sep. 16, 2015, now Pat. No. 10,117,891.

(60) Provisional application No. 62/050,864, filed on Sep. 16, 2014.

(51) Int. Cl.
| | |
|---|---|
| *A61K 31/714* | (2006.01) |
| *A61K 31/352* | (2006.01) |
| *A61K 9/00* | (2006.01) |
| *A61K 31/05* | (2006.01) |
| *A61K 36/185* | (2006.01) |
| *A61K 47/44* | (2017.01) |

(52) U.S. Cl.
CPC .......... *A61K 31/714* (2013.01); *A61K 9/0014* (2013.01); *A61K 31/05* (2013.01); *A61K 31/352* (2013.01); *A61K 36/185* (2013.01); *A61K 47/44* (2013.01)

(58) Field of Classification Search
CPC .... A61K 31/714; A61K 31/05; A61K 31/352; A61K 36/185; A61K 9/0014; A61K 47/44
See application file for complete search history.

(56) References Cited

U.S. PATENT DOCUMENTS

| | | |
|---|---|---|
| 5,240,937 A | 8/1993 | Kelley |
| 5,391,740 A | 2/1995 | Wang et al. |
| 6,503,532 B1 | 1/2003 | Murty |
| 6,683,086 B2 | 1/2004 | Druzgala et al. |
| 6,949,582 B1 | 9/2005 | Wallace |
| 8,859,540 B2 | 10/2014 | Rundfeldt et al. |
| 2004/0043043 A1 | 3/2004 | Schlyter et al. |
| 2004/0138293 A1 | 7/2004 | Werner et al. |
| 2005/0042172 A1 | 2/2005 | Whittle |
| 2006/0127499 A1 | 6/2006 | Lazarev et al. |
| 2006/0257502 A1 | 11/2006 | Liu |
| 2007/0293440 A1 | 12/2007 | Smith-Swintosky et al. |
| 2007/0293476 A1 | 12/2007 | Smith-Swintosky et al. |
| 2008/0254017 A1 | 10/2008 | Kane et al. |
| 2010/0035978 A1 | 2/2010 | Guy et al. |
| 2011/0065627 A1 | 3/2011 | Barathur |
| 2011/0217278 A1 | 9/2011 | Felder |
| 2011/0301238 A1 | 12/2011 | Borges |
| 2012/0004251 A1 | 1/2012 | Whalley et al. |
| 2012/0165402 A1 | 6/2012 | Whalley et al. |
| 2012/0322782 A1 | 12/2012 | Narishetty et al. |
| 2013/0065898 A1 | 3/2013 | Rundfeldt et al. |
| 2013/0296398 A1 | 11/2013 | Whalley et al. |
| 2013/0309306 A1 | 11/2013 | Rogawski et al. |
| 2014/0050789 A1 | 2/2014 | Bogawski et al. |
| 2014/0155456 A9 | 6/2014 | Whalley et al. |
| 2014/0243405 A1 | 8/2014 | Whalley et al. |

(Continued)

FOREIGN PATENT DOCUMENTS

| | | |
|---|---|---|
| CA | 2424356 A | 4/2003 |
| WO | WO 2001/00196 A2 | 1/2001 |

(Continued)

OTHER PUBLICATIONS

Grotenhermen, F., Clin. Pharmacokinet. 2003, 42(4), p. 327-360. (Year: 2003).*
U.S. Appl. No. 15/104,556, filed Jun. 15, 2016 (pending).
International Application S.N. PCT/US2017/037394, filed Jun. 14, 2017 (pending).
PCT Search Report dated Dec. 10, 2015, in International App. S.N. PCT/US2015/050342, filed Sep. 16, 2015 (9 pages).
PCT Search Report dated Mar. 16, 2016, in International App. S.N. PCT/US2016/013323, filed Jan. 14, 2016 (8 pages).
PCT Search Report dated Jun. 17, 2016, in International App. S.N. PCT/US2016/24145, filed Mar. 25, 2016 (10 pages).

(Continued)

*Primary Examiner* — Jonathan S Lau
(74) *Attorney, Agent, or Firm* — Studebaker & Brackett PC

(57) ABSTRACT

A combination of THC, CBD and Cobalamin (in a ratio of about 63%, 27% and 10%, respectively) is used with a topical carrier such as Shea butter cream to relieve pain. The THC and CBD mixture is extracted from a *Cannabis indica* dominant strain using high pressure and carbon dioxide ($CO_2$) as a solvent and comprises: Tetrahydrocannabinol "THC" (9-Tetrahydrocannabinol (delta-9 THC), 8-Tetrahydrocannabinol (Delta-8 THC) and 9-THC Acid), Cannabidiol "CBD", Cannabinol "CBN", Cannabichromene ("CBC), Cannabigerol ("CBG"), terpenoids and flavonoids. The Shea butter is an extract from the Shea nut from the Shea tree (*Vitellaria paradoxa*). The weight of THC, CBD and Cobalamin, excluding other ingredients in the *Indica* extract, is in the range of about 1.0% to 5% of the total weight of the Shea butter. The cream is applied to joints for indications such as Psoriatic Arthritis and Scleroderma. The mixture is absorbed through the skin and interacts with the peripheral nervous and immune systems via the A Delta and C nerve fibers and CB 2 skin receptors to provide relief from pain without psychotropic or other side effects normally associated with THC.

15 Claims, No Drawings

(56) References Cited

U.S. PATENT DOCUMENTS

| | | |
|---|---|---|
| 2014/0348926 A1 | 11/2014 | Hoffman et al. |
| 2015/0086494 A1 | 3/2015 | Sekura et al. |
| 2015/0265637 A1 | 9/2015 | Kane et al. |
| 2015/0359756 A1 | 12/2015 | Guy et al. |
| 2017/0027978 A1 | 2/2017 | Mukunda et al. |

FOREIGN PATENT DOCUMENTS

| | | |
|---|---|---|
| WO | WO 02/064109 A2 | 8/2002 |
| WO | WO 2004/075896 A1 | 9/2004 |
| WO | WO 2010/048423 A1 | 4/2010 |
| WO | WO 2011/063164 A2 | 5/2011 |
| WO | WO 2011/110866 A1 | 9/2011 |
| WO | WO 2014/145490 A2 | 9/2014 |
| WO | WO 2016/044370 A1 | 3/2016 |
| WO | WO 2016/059399 A1 | 4/2016 |
| WO | WO 2016/118391 A1 | 7/2016 |
| WO | WO 2016/160542 A1 | 10/2016 |
| WO | WO 2017/027651 A1 | 2/2017 |
| WO | WO 2017/218629 A1 | 12/2017 |
| WO | WO 2018/160510 A1 | 9/2018 |

OTHER PUBLICATIONS

PCT Search Report dated Oct. 31, 2016, in International App. S.N. PCT/US2016/46451, filed Aug. 11, 2016 (9 pages).

PCT Search Report dated Aug. 31, 2017, in International App. S.N. PCT/US2017/037394, filed Jun. 14, 2017 (10 pages).

Seimens et al., Effect of cannabis on pentobarbital-induced sleeping time and pentobarbital metabolism in the rat, Biochemical Pharmacology, vol. 23: 477-488, 1974 [retrieved on Feb. 25, 2016]. Retrieved from the internet :<URL: http://www.sciencedirect.com/science/article/pii/0006295274906121>abstract.

Schlanger, S et al., Diet Enriched with Omega-3 Fatty Acids Alleviates Convulsion Symptoms in Epilepsy Patients. Epilepsia. 2002. vol. 43. No. 1; abstract; p. 103, first-second columns; p. 104, first column.

McMahan, K. Hemp Seed Oil—Why Should We Use It? Monterey Bay Hollistic Alliance. 2014; https://montereybayhollistic.wordpress.com/2014/08/23/hemp-seed-oil/; pp. 1-2, 4.

Kardinal. CG et al. Controlled trial of cyproheptadine in cancer patients with anorexia and/or cachexia. Cancer. Jun. 15, 1990. vol. 65. pp. 2657-2662; abstract; p. 2659. left column, 2nd, 4th paragraphs; p. 2661, right column, 2nd paragraph; table 5.

U.S. Appl. No. 15/751,901, filed Feb. 12, 2018 (pending) (readily available from the USPTO records).

Office Action dated May 15, 2018 in U.S. Appl. No. 15/104,556, filed Jun. 16, 2016 (pending) (readily available from the USPTO records).

EPO Search Report dated Apr. 12, 2018, in European Application No. EP 15841994.5, filed Sep. 16, 2015 (7 pp.)

Anonymous: "Vitamin B12-Essential for Chronic Pain Management", May 9, 2014 (May 9, 2014), XP055464506, Retrieved from the Internet: URL:http://blog.vitasciences.com/chronic-pain/vitamin-b12-essential-for-chronic-pain-management/ [retrieved on Apr. 4, 2018].

International Application S.N. PCT/US2018/019814, filed Feb. 27, 2018 (pending).

PCT Search Report dated Apr. 20, 2018 in International App. S.N. PCT/US2018/019814, filed Feb. 27, 2018 (11 pages).

McPartland et al., J. Cannabis Ther., 2001, 1(3-4), p. 103-132 (Year: 2001).

\* cited by examiner

CANNABINOID COMPOSITION AND METHOD FOR TREATING PAIN

CROSS-REFERENCE TO RELATED APPLICATIONS

This application is a divisional of application Ser. No. 15/104,554, filed Jun. 15, 2016, now U.S. Pat. No. 10,117,891, which is a 371 (35 USC 371) of International Application S.N. PCT/US2015/050342, filed Sep. 16, 2015, which claims priority on prior U.S. Provisional Application Ser. No. 62/050,864, filed Sep. 16, 2014, all of which are hereby incorporated herein in their entirety by reference.

FIELD OF THE INVENTION

This invention relates to compositions and methods for relieving pain using cannabinoids and cobalamin. The invention is especially useful for relieving pain in patients with psoriatic arthritis, fibromyalgia, scleroderma, shingles and related pain generating conditions.

BACKGROUND OF THE INVENTION

The American Pain Society recommends that pain be made more visible and categorized as the fifth vital sign. Terminal illnesses are often accompanied by unbearable pain that is severe and difficult to treat.

Physicians are often reluctant to administer large doses of analgesic drugs for fear of respiratory depression or other complications. The same holds true for currently available opioid-based drug therapies which can produce undesirable side effects such as hallucinations, constipation, sedation, nausea and dysphoria.

Pain management is a great challenge for health care professionals as pain often can debilitate individuals in ways that affects their day-to-day functioning and productivity. Arthritis, for example, has been particularly problematic for women. Since 1999 there has been a 22 percent increase in the number of women who attribute their disability to arthritis.

Health economists writing in The Journal of Pain in September 2012, reported that the annual estimated national cost of pain management ranges from $560 billion to $635 billion.

The literature has reported the use of *cannabis* to treat pain and the use of methylcobalamin to treat peripheral neuropathy:
1. Stander, S., M., Schmelz, D. Metze, T. Luger, and R. Rukwied. "Distribution of cannabinoid receptor 1 (CB1) and 2 (CB2) on sensory nerve fibers and adnexal structures in human skin" Journal of Dermatological Science 38.3 (2005): 177-188
2. Manzanares, J., M. Julian and A. Carrascosa. "Role of the Cannabinoid System in Pain Control and Therapeutic Implications for the Management of Acute and Chronic Pain Episodes" Current Neuropharmocology. 4.3 (2006): 239-257
3. Jorge, L. L., C. C. Feres and V. E, Teles. "Topical preparations for pain relief: efficacy and patient adherence" Journal of Pain Research. 4 (2011): 11-24.
4. Wantanabe, T., R. Kaji, N. Oka, W. Bara and J. Kimura. "Ultra-high dose methylcobalamin promotes nerve regeneration in experimental acrylamide neuropathy" Journal of the neurological sciences 122.2 (1994): 140-143
5. Naik, S. U. and D. V. Sonawane. "Methylcobalamine is effective in peripheral neuropathies." *European journal of clinical nutrition* (2015).

SUMMARY OF THE INVENTION

The invention provides compositions and methods for treating pain by administering to a patient in pain a composition comprising: (i) tetrahydrocannabinol (THC); (ii) cannabidiol (CBD); and (iii) cobalamin. The invention is especially useful for relieving pain in patients with psoriatic arthritis, fibromyalgia, scleroderma, shingles and related pain generating conditions.

An important aspect of the invention is the unexpected absence of side effects such as hallucinations, constipation, sedation, nausea, respiratory depression and dysphoria or other undesirable side effects.

The composition can be administered orally or topically with a topical carrier and the individual ingredients can be administered separately.

While THC is used in an amount greater than CBD and cobalamin is used in an amount less than either of THC or CBD, it is preferred that THC be used in an amount greater than 50% by weight, CBD in an amount up to about 30% by weight and cobalamin in an amount up to about 20% by weight.

In a preferred embodiment, THC is used in an amount from about 50% to about 70% by weight, CBD in an amount from about 20% to about 40% by weight and cobalamin in an amount from about to about 20% by weight. In a further preferred embodiment, THC is used in an amount of about 63% by weight, CBD in an amount of about 27% and cobalamin in an amount of about 11%.

Preferred THC and CBD are extracted from *Cannabis Indica* or *Cannabis Sativa* or can be entirely synthetic. CBD can also be so-called organic which contains lesser or trace amounts of cannabinol (CBN), cannabichromene (CBC), cannabigerol (CBG), terpenoids and flavonoids.

DETAILED DESCRIPTION OF THE INVENTION

THC, CBD and cobalamin for topical application are used with a topical carrier such as Shea butter cream. Other topical oils and creams are known and include coconut oil, sesame oil and the like.

THC and CBD can be used in their pure, synthetic form or as a mixture of compounds that result from extracting *Cannabis Indicia* or *Cannabis Sativa*. Such mixtures contain CBD, THC (which in turn is a mixture comprising 9-tetrahydrocannabinol (delta-9 THC), 8-tetrahydrocannabinol (delta-8 THC) and 9-THC Acid)), cannabinol (CBN), cannabichromene (CBC), cannabigerol (CBG), terpenoids and flavonoids.

The preferred THC-CBD mixture is extracted from a *Cannabis Indica* dominant strain using high pressure and carbon dioxide as a solvent in a 1500-20 L subcriticalisupercritical $CO_2$ system made by Apeks Super Critical Systems, 14381 Blamer Rd., Johnstown, Ohio, 43031. See http://www.apekssupercritical.com/botanical-extraction-systems/

Apeks Systems use valveless expansion technology with no constrictions or regulating valves to cause clogging in the system between the extraction vessel and the $CO_2$ expansion separator. Flow of liquid $CO_2$ and dissolved oil travels from the extraction vessel into the separator, and the oil is separated from the $CO_2$ in the separator/collection vessel.

CO2 is recycled during the extraction process and recovered and regenerative heat capture methods are used to increase efficiency.

A further process using solvents can be used to remove THC from the mixture leaving either pure CBD or so-called "organic CBD" containing CBD and lesser or trace amounts of CBN, CBC, CBG, terpenoids and flavonoids.

Another source of CBD essentially free of THC is the CBD mixture obtained by extracting hempseed oil. See Leizer et al, J. Nutraceuticals, Functional and Medical Foods, Vol. 2(4) 2000, The Haworth Press, Inc. Elixinol (D&G Health LLC) is a predominantly CBD product extracted from hempseed oil that contains trace amounts of THC.

Cabalamin refers to several chemical forms of vitamin B12. The active form of cobalamin (methylcobalamin) is preferred and other forms, such as adenosylcobalamin, can also be used.

The Shea butter is an extract from the Shea nut from the Shea tree (*Vitellaria paradoxa*). The weight of THC, CBD and Cobalamin, excluding other ingredients in the *Indica* extract, is in the range of about 1.0% to 5% of the total weight of the Shea butter.

The inventive composition can be used to treat pain associated with a number of conditions including fibromyalgia, scleroderma, trigeminal neuralgia, psoriatic arthritis, critical illness neuropathy and other similar conditions.

These conditions are believed to mediate pain via the alpha delta and x nerve fibers when the myelin sheath of such fibers becomes myelinated (loose myelin). Myelin is primarily composed of B 12 and cholesterol. It is believed that B12 acts synergistically in the inventive composition to restore and maintain myelin sheath integrity of the nerve fibers, and, at the same time, enhancing pain relief without the undesirable side effects of opioids and chemotherapeutic agents.

Topical cream is applied to joints for indications such as psoriatic arthritis, herpetic neuralgia, trigeminal neuralgia, reflex sympathetic dystrophy, complex regional pain syndrome, terminal neuralgia, scleroderma and other conditions where pain is present. The mixture is absorbed through the skin and interacts with the peripheral nervous and immune systems via the a delta and x nerve fibers and CB 1 and CB 2 skin receptors to provide relief from pain without psychotropic or other side effects normally associated with THC.

The Composition of the invention can also be delivered to affected joints and other areas of the skin using bio patches which can cover an area of the skin to which the cream has been applied or the cream can first be applied to the patch before being placed on a patient.

Useful patches include transdermal Nusil patches using a pressure-sensitive adhesive or a strong-tack silicone gel, patches employing hydrophobic porous transfer adhesive (available from Adhesives Research, Inc., Glen Rock, Pa.), and medical-grade adhesives and tapes for wound care in the form of single-coated film tapes, single-coated foam tapes, single-coated non-woven tapes, single-coated hydrocolloid film tapes, and hydrocolloid transfer tapes made by, for example, Avery Dennison Medical, Mentor, Ohio. Other useful bio-patches are available from: Brady Medical Solutions, Mesquite, Tex.; Yulex Corp., Maricopa, Ariz.; and Labtech GmbH, Langenfeld, Germany.

Example 1

Organic, pesticide free female *Indica* dominant strain buds were extracted using an Apeks 1500-20 L high pressure, carbon dioxide based extractor and heat to yield an oil high in THC. CBD was extracted using the same Apeks system from a different strain of *Indicia cannabis* using a similar process. Each Apeks extraction was carried out using 1200 psi $CO_2$ in the extractor and 300 psi $CO_2$ in the separator with the chiller at 64° F.

7.2 mg of THC (along with delta 8 THC, 9-THC acid), cannabinol (CBN), cannabichromene (CBC), cannabigerol (CBG), terpenoids and flavonoids present in the extract) was mixed with 3 mg of CBD and 1.2 mg of cobalamin to yield 11.4 mg of drug which was then mixed with 988.6 mg of Shea butter (an extract from the Shea nut from the Shea tree (*Vitellaria paradoxa*)). 1,000 mg of cream was available for topical application.

Studies were conducted on patients with severe arthritic pain using a self-assessed Numeric Rating Scale (NRS-11). The scale describes pain levels, as shown in the table below:

| Rating | Pain Level |
|--------|------------|
| 0 | No Pain |
| 1-3 | Mild Pain (nagging, annoying) |
| 4-6 | Moderate pain (interferes significantly with daily life |
| 7-10 | Severe pain (disabling, unable to perform tasks) |

Example 2

20 mg of the cream prepared in Example 1 was applied to the left wrist joint and fingers including the knuckles of a patient with severe arthritic pain. Prior to the application of the cream the patient reported a NRS-11 score between five and seven. About six minutes after application of the cream the patient reported a NRS-11 score between zero and two. The relief lasted five hours. There were no side effects.

Example 3

30 mg of the cream prepared in Example 1 was applied to an Adhesives Research, Inc. patch which was applied to the left wrist joint and fingers including the knuckles of a patient with severe arthritic pain. Prior to the application of the cream the patient reported a NRS-11 score between six and seven. Subsequent to the application of the patch the patient reported a NSR-11 score between zero and two. The relief lasted about seven hours, There were no side effects.

Example 4

30 mg of the cream prepared in Example 1 was applied to a Nusil patch which was applied to the left wrist joint and fingers including the knuckles of a patient with severe arthritic pain. Prior to the application of the cream the patient reported a NRS-11 score between six and seven.

Subsequent to the application of the patch the patient reported a NRS-11 score between zero and two. The relief lasted about five hours. There were no side effects.

Those skilled in the art will recognize, or be able to ascertain many equivalents to the specific embodiments of the invention described herein.

It will be understood that the invention is capable of further modifications, uses and/or adaptations including such departures within the known or customary practice in the art to which the invention pertains. The invention is not limited to the preferred embodiments described herein.

What is claimed is:

1. Method for treating pain comprising administering to a patient in need thereof:
   (i) tetrahydrocannabinol (THC) in an amount from about 50% to about 70% by weight,
   (ii) cannabidiol (CBD) in an amount from about 20% to about 40% by weight,
   (iii) cobalamin in an amount from about 5% to about 20% by weight, and
   (iv) a carrier;
wherein each percentage amount of THC, CBD and cobalamin is based on total weight of THC, CBD and cobalamin.

2. Method of claim 1 wherein THC is used in an amount greater than CBD and cobalamin is used in an amount less than either of THC or CBD.

3. Method of claim 1 wherein THC is used in an amount greater than 50% by weight, CBD in an amount up to about 30% by weight and cobalamin in an amount up to about 20% by weight.

4. Method of claim 1 wherein THC and CBD are extracted from *Cannabis sativa*.

5. Method of claim 1 wherein THC and or CBD are synthetic.

6. Method of claim 1 wherein CBD is organic CBD also containing cannabinol (CBN), cannabichromene (CBC), cannabigerol (CBG), terpenoids and flavonoids.

7. Method of claim 1 wherein THC, CBD and cobalamin are administered separately.

8. Method of claim 1 wherein THC is in the amount of about 63% by weight, CBD is in the amount of about 27% by weight and cobalamin is in the amount of about 11% by weight.

9. Method of claim 1 wherein THC and CBD are extracted from *Cannabis indica*.

10. Method of claim 9 wherein THC and CBD are extracted in an oil dissolved in liquid $CO_2$, then the oil is separated therefrom.

11. Method of claim 1 wherein CBD is extracted from hempseed oil.

12. Method of claim 1 wherein the carrier is Shea butter.

13. Method of claim 12 wherein total weight of THC, CBD and cobalamin is about 1.0% to 5% of Shea butter's weight.

14. Method of claim 1 wherein a topical cream of THC, CBD, cobalamin and carrier is applied to a joint of the patient for the pain of psoriatic arthritis, herpetic neuralgia, trigeminal neuralgia, reflex sympathetic dystrophy, complex regional pain syndrome, or scleroderma.

15. Method of claim 1 wherein a patch delivers THC, CBD, cobalamin and carrier to an affected joint or area of skin of the patient.

* * * * *